United States Patent
Ouchi

(10) Patent No.: US 6,262,289 B1
(45) Date of Patent: Jul. 17, 2001

(54) PROCESS FOR PREPARING CYCLIC OLIGOSILOXANES

(75) Inventor: Katsuya Ouchi, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/445,417

(22) PCT Filed: Jun. 10, 1998

(86) PCT No.: PCT/JP98/02562

§ 371 Date: Dec. 8, 1999

§ 102(e) Date: Dec. 8, 1999

(87) PCT Pub. No.: WO98/56795

PCT Pub. Date: Dec. 17, 1998

(30) Foreign Application Priority Data

Jun. 11, 1997 (JP) ................................................ 9-153613
Jul. 29, 1997 (JP) ................................................ 9-202889

(51) Int. Cl.⁷ ................................................ C07F 7/08
(52) U.S. Cl. ........................ 556/451; 556/460; 556/461
(58) Field of Search .................................. 556/451, 460, 556/461

(56) References Cited

U.S. PATENT DOCUMENTS

| | | |
|---|---|---|
| 2,438,478 | 5/1948 | Hyde . |
| 2,455,999 | 12/1948 | Hyde . |
| 3,558,681 | 1/1971 | Kuznetsova et al. . |
| 4,507,469 | 3/1985 | Mita et al. . |
| 5,395,956 | 3/1995 | Haines et al. . |
| 5,420,325 | 5/1995 | Razzano . |
| 5,491,249 | 2/1996 | Kostas . |

FOREIGN PATENT DOCUMENTS

| | | |
|---|---|---|
| 1086518 | 5/1994 | (CN) . |
| 31-2171 | 4/1930 | (JP) . |
| 33-2149 | 4/1956 | (JP) . |
| 35-4240 | 4/1960 | (JP) . |
| 36-17196 | 9/1961 | (JP) . |
| 45-15036 | 5/1970 | (JP) . |
| 46-34118 | 10/1971 | (JP) . |
| 47-8646 | 5/1972 | (JP) . |
| 48-12399 | 2/1973 | (JP) . |
| 49-92095 | 9/1974 | (JP) . |
| 50-100075 | 8/1975 | (JP) . |
| 54-90120 | 7/1979 | (JP) . |
| 54-117491 | 9/1979 | (JP) . |
| 55-38898 | 3/1980 | (JP) . |
| 55-98190 | 7/1980 | (JP) . |
| 59-73592 | 4/1984 | (JP) . |
| 59-222495 | 12/1984 | (JP) . |
| 61-161289 | 7/1986 | (JP) . |
| 62-119232 | 5/1987 | (JP) . |
| 62-35421 | 8/1987 | (JP) . |
| 62-227930 | 10/1987 | (JP) . |
| 1-216999 | 8/1989 | (JP) . |
| 2-129192 | 5/1990 | (JP) . |
| 2-191286 | 7/1990 | (JP) . |
| 6-16683 | 1/1994 | (JP) . |
| 6-80680 | 3/1994 | (JP) . |
| 6-287196 | 10/1994 | (JP) . |
| 6-312996 | 11/1994 | (JP) . |
| 7-102066 | 4/1995 | (JP) . |
| 7-242678 | 9/1995 | (JP) . |
| 7-285974 | 10/1995 | (JP) . |
| 7-316167 | 12/1995 | (JP) . |
| 8-109187 | 4/1996 | (JP) . |
| 8-176162 | 7/1996 | (JP) . |
| 8-291220 | 11/1996 | (JP) . |
| 9-48787 | 2/1997 | (JP) . |

OTHER PUBLICATIONS

Winton Patnode et al., "Methylpolysiloxanes", Research Laboratory of General Electric, Mar. 1946, vol. 68, pp. 358–363.

M. J. Hunter et al., "Organo–Silicon Polymers. The Cyclic Dimethyl Siloxanes", Dow Corning Corporation, Apr. 1946, pp. 667–672.

P.V. Wright et al., "Equilibrium ring concentrations and the statistical conformations of polymer chains: Part 3. Substituent effects in polysiloxane systems", *Polymer*, vol. 11, 1970, pp. 462–471.

Wayne A. Gustavson et al., "Redistribution Reactions of Methylsiloxanes Catalyzed by Transition Metal Complexes", *Journal of Organometallic Chemistry*, 238 (1982), pp. 87–97.

J.V. Crivello et al., "Synthesis of Cyclic Siloxanes by the Thermal Depolymerization of Linear Poly(siloxanes)", *Chemistry of Materials*, 1989, vol. 1, pp. 445–451.

Pao–Sun Chang et al., "Synthesis of Cyclooligomers via the Living Depropagation of Poly(dimethylsiloxane–co–methylhydrogensiloxane)", *Chem. Mater.*, vol. 5, 1993, pp. 983–988.

*Primary Examiner*—Paul F. Shaver
(74) *Attorney, Agent, or Firm*—Armstrong, Westerman, Hattori, McLeland & Naughton, LLP

(57) ABSTRACT

This invention is a method for the production of a cyclic oligosiloxane, which comprises heating a linear or cyclic polysiloxane in the presence of a metal alkoxide, by which the cyclic oligosiloxane can be produced with high yield by a method having industrially high practical value, because it can carry out the reaction under moderate conditions without causing gelation of the reaction system, in comparison with conventional methods using an alkaline or acidic catalyst.

16 Claims, No Drawings

PROCESS FOR PREPARING CYCLIC OLIGOSILOXANES

TECHNICAL FIELD

This invention relates to a method for the production of a cyclic oligosiloxane represented by formula (III):

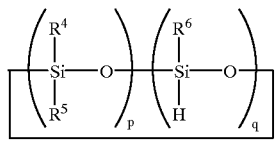

(III)

which is used as a material in the field of silicone industry.

BACKGROUND ART

Regarding disproportionation of polysiloxane, a method in which an acidic or alkaline catalyst is used is generally known. However, such an acidic or alkaline catalyst-aided method is not advantageous for industrially stable production because of the severe reaction conditions. Formation of cyclosiloxane by heat decomposition of polysiloxane is known as an example of disproportionation method under neutral condition, but this method requires an extremely high temperature of about 300° C. so that this cannot also be regarded as an advantageous method for industrially stable production. As another disproportionation method under neutral condition, a method in which a transition metal catalyst is used is known, but since this method requires the use of a catalyst of Pt, Pd or the like expensive metal, this cannot be said as an industrially advantageous method when such a costly point of view is taken into consideration.

Cyclic oligosiloxane compounds are used as materials for the production of high molecular weight polysiloxane compounds in the field of silicone industry. Also, a cyclic oligosiloxane containing Si—H group is used as a material for the production of room temperature crosslinking type silicone rubber which is used for example in sealant in the field of silicone industry. The room temperature crosslinking type silicone rubber is obtained by crosslinking the cyclic oligosiloxane containing Si—H group with a polysiloxane containing vinyl group through their reaction in the presence of a platinum catalyst. The cyclic oligosiloxane containing Si—H group is also used as a material for the production of an organic functional group-linked oligosiloxane which is used for example as an adhesive property increasing agent. The organic functional group-linked oligosiloxane is obtained by allowing the cyclic oligosiloxane containing Si—H group to react with a vinyl group-containing organic group in the presence of a platinum catalyst.

As a generally known method for the production of cyclic oligosiloxane, a method of hydrolysis condensing organosilanes having two hydrolyzable groups on its silicon atoms such as dimethyldichlorosilane or the like compound. However, this method is not advantageous for its industrially stable production, because the reaction system becomes acidic severe condition under such hydrolysis condensation condition.

Particularly, in the case of the production of the cyclic oligosiloxane containing Si—H group, the Si—H group has considerably high reactivity under such acidic condition and therefore reacts with water or silanol group coexisting in the reaction system, so that yield of the compound of interest becomes low. Accordingly, the following methods (a) and (b) have been proposed for dissolving this problem.

Namely, (a) a method in which methyldichlorosolane is hydrolyzed in the presence of a mixed solvent of tetrahydrofuran with a hydrocarbon solvent (JP-A-6-80680; the term "JP-A" as used herein means an "unexamined published Japanese patent application") and (b) a method in which dichlorodisiloxane is hydrolyzed in the presence of t-butyl alcohol (JP-A-7-285974).

However, it is necessary to use benzene as the hydrocarbon solvent in the aforementioned method (a) in order to obtain a cyclic oligosiloxane as the product with a high yield, but industrial realization of this method may cause a problem in terms of the safety for benzene. Also, dichlorodisiloxane to be used as a material in the aforementioned method (b) is not a material commercialized as a generalized product, so that availability of this material generally becomes a problem when this method is carried out, as well as a problem of lacking in the flexibility of industrial techniques.

In addition, chlorosilane is hydrolyzed in each of the methods (a) and (b), but it is known that hydrogen chloride is formed as a by-product by this reaction and the product is contaminated by a small amount of hydrogen chloride. However, when such a product containing hydrogen chloride is used for example in electronic materials, the final product containing ion components such as chloride ion is not desirable from the viewpoint, for example, of the corrosion of electrodes. Thus, the products manufactured by such methods are not suited for their application to electronic materials and the like, and their industrial availability is reduced. Also, the reaction is carried out under strongly acidic condition in each of the methods (a) and (b), so that not only the steps become complex, such as adjustment of pH in the after step, but also it causes a problem in that caution is required in handling the material.

As other methods for the production of cyclic oligosiloxane, certain methods have been proposed in which a linear polysiloxane or a high polymerization degree cyclic polysiloxane is subjected to its reaction under various conditions in the presence of an acidic or alkaline catalyst.

Examples of the method which uses an acidic catalyst include (c) a method in which polysiloxane containing Si—H group is subjected to the reaction in the presence of water and activated clay (JP-B-54-13480; the term "JP-B" as used herein means an "examined Japanese patent publication"), (d) a method in which methylhydrogenpolysiloxane is subjected to the reaction by heating it in the presence of an acid catalyst (JP-B-55-11697), (e) a method in which organopolysiloxane is subjected to the reaction by allowing it to contact with a heated fixed catalyst bed under a reduced pressure (JP-A-2-129192), (f) a method in which the reaction of methylhydrogenpolysiloxane is carried out in the presence of a high boiling point organodisiloxane (JP-A-7-242678) and (g) a method in which organohydrogenpolysiloxane is subjected to the reaction in the presence of aluminum chloride (JP-A-7-316167).

However, the aforementioned method (c) has an industrially serious problem of causing gelation of the reaction system due to high reactivity of the Si—H group with water under acidic condition. The aforementioned methods (d) and (e) require a considerably high temperature of from 250 to 500° C. for the reaction, thus causing a problem when used in an industrial scale. In the aforementioned method (f), it is necessary to use a high boiling point disiloxane as a side material in addition to the main material. However, such a special disiloxane is not a material commercialized as a generalized product, so that this method lacks in the flexibility of industrial techniques in terms of the availability of the material when this method is carried out. It also is not industrially advantageous from the viewpoint of cost.

In addition, each of the aforementioned methods (c) to (g) uses an acid catalyst. Particularly, the aforementioned method (g) uses aluminum chloride as the catalyst having considerably strong acidity. Also, since Si—H group is basically unstable against water and the like under acidic condition, it is not desirable to use an acid catalyst in the Si—H group-containing system of these methods; for example, when the reaction system is contaminated by even a small amount of water for example from the material or air, the Si—H group reacts with water to decrease yield of the cyclic oligosiloxane as the product and also to cause gelation of the reaction system. In consequence, the aforementioned methods (c) to (g) which use acid catalysts are techniques that have practical problems from the viewpoint of stable industrial production.

Examples of the method in which an alkaline catalyst is used include (h) a method in which carbonate of an alkali metal is used as the catalyst (JP-B-45-15036) and (i) a method in which an alkali metal silanolate is used as the catalyst (JP-B-33-2149).

However, since these methods use alkaline catalysts, not only the steps become complex, such as adjustment of pH in the after step, but also caution is required in handling the materials, similar to the case of acid catalysts, so that they have a problem in terms of stable industrial production. In addition, since the Si—H group in the Si—H group-containing system is considerably unstable under alkaline condition, these methods cannot substantially be used. Thus, the aforementioned methods (h) and (i) which use alkaline catalysts are techniques that have practical problems from the viewpoint of stable industrial production and also lack in flexibility.

In consequence, in order to resolve the aforementioned problems, the present invention aims at providing a method for the production of cyclic oligosiloxane, which is practical in carrying out industrial production because a material available with low cost is used, the reaction can be carried out under moderate conditions, namely neutral condition and relatively low temperature, and, particularly, gelation of the reaction system does not occur in the case of a system which contains Si—H group.

DISCLOSURE OF THE INVENTION

As a result of the extensive investigation to resolve the above-mentioned problems, the inventors of the present invention have found that a cyclic oligosiloxane can be practically produced by carrying out the reaction in the presence of a metal alkoxide, thereby resulting in the accomplishment of this invention.

Accordingly, the present invention includes a method for producing a cyclic oligosiloxane, which comprises heating a linear or cyclic polysiloxane in the presence of a metal alkoxide (claim 1);

a method for producing a cyclic oligosiloxane represented by formula (III):

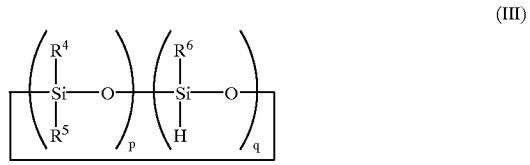

(wherein $R^4$ to $R^6$ may be the same or different from one another and each represents a monovalent substituted or unsubstituted hydrocarbon radical, p and q are each independently 0 or a number of from 1 to 10, and p and q are also numbers that satisfy $3 \leq p+q \leq 10$), which comprises heating a linear polysiloxane represented by formula (I):

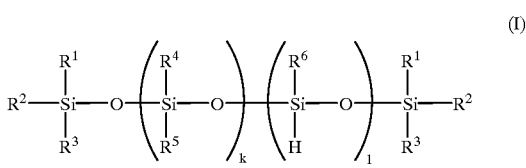

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ to $R^6$ may be the same or different from one another and each represents a monovalent substituted or unsubstituted hydrocarbon radical, k and l are each independently 0 or a number of from 1 to 1,000, and k and l are also numbers that satisfy $4 \leq k+l \leq 1,000$) and/or a cyclic polysiloxane represented by formula (II):

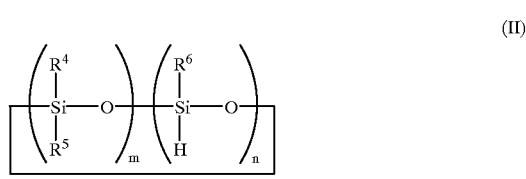

(wherein $R^4$ to $R^6$ may be the same or different from one another and each represents a monovalent substituted or unsubstituted hydrocarbon radical, m and n are each independently 0 or a number of from 1 to 1,000, and m and n are also numbers that satisfy $3 \leq m+n \leq 1,000$) in the presence of a metal alkoxide (claim 2);

the method for producing a cyclic oligosiloxane according to claim 2, wherein k and m are each independently 0 or a number of from 1 to 999, l and n are each independently a number of from 1 to 1,000, p is 0 or a number of from 1 to 9 and q is a number of from 1 to 10 (claim 3);

the method for producing a cyclic oligosiloxane according to claim 3, wherein k, l, m, n, p and q are numbers which satisfy $5 \leq m+n \leq 1,000$, p+q<k+l and p+q<m+n (claim 4);

the method for producing a cyclic oligosiloxane according to any one of claims 2 to 4, wherein each of $R^1$, $R^4$ and $R^6$ is a methyl group, $R^2$ is a hydroxyl group or a methyl group and $R^3$ is a hydrogen atom or a methyl group (claim 5);

the method for producing a cyclic oligosiloxane according to any one of claims 2 to 5, wherein k, l, m, n, p and q are k<l, m<n and p<q (claim 6);

the method for producing a cyclic oligosiloxane according to any one of claims 3 to 5, wherein k=m=p=0 (claim 7), a method for producing a cyclic oligosiloxane represented by formula (VIII):

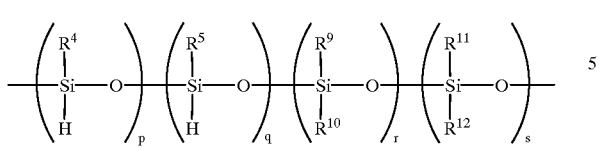

(VIII)

(wherein $R^4$, $R^5$, $R^9$, $R^{10}$, $R^{11}$ and $R^{12}$ may be the same or different from one another and each represents a monovalent substituted or unsubstituted hydrocarbon radical, each of p, q, r and s is a number of from 0 to 9, and p, q, r and s are also numbers that satisfy $3 \leq p+q+r+s \leq 10$, $1 \leq p+q$ and $1 \leq r+s$), which comprises heating (1) a polysiloxane component consisting of a linear polysiloxane represented by formula (IV):

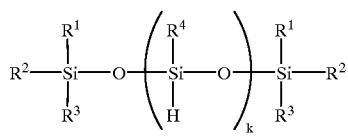

(IV)

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ represents a monovalent substituted or unsubstituted hydrocarbon radical, and k is a number of from 4 to 1,000) and/or a cyclic polysiloxane represented by formula (V):

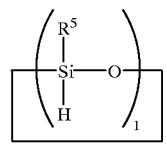

(V)

(wherein $R^5$ represents the same or a different monovalent substituted or unsubstituted hydrocarbon radical, and l is a number of from 4 to 1,000) and (2) a polysiloxane component consisting of a linear polysiloxane represented by formula (VI):

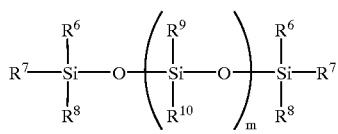

(VI)

(wherein $R^6$ represents a hydroxyl group or a monovalent substituted or unsubstituted hydrocarbon radical, $R^7$ to $R^{10}$ may be the same or different from one another and each represents a monovalent substituted or unsubstituted hydrocarbon radical, and m is a number of from 4 to 1,000) and/or a cyclic polysiloxane represented by formula (VII):

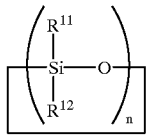

(VII)

(wherein $R^{11}$ and $R^{12}$ may be the same or different from each other and each represent a monovalent substituted or unsubstituted hydrocarbon radical, and n is a number of from 4 to 1,000), in the presence of a metal alkoxide (claim 8);

a method for producing a cyclic oligosiloxane represented by formula (IX):

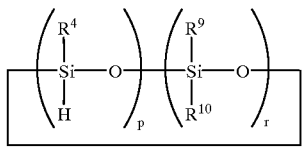

(IX)

(wherein $R^4$, $R^9$ and $R^{10}$ may be the same or different from one another and each represents a monovalent substituted or unsubstituted hydrocarbon radical, each of p and r is a number of from 1 to 9, and p and r are also numbers that satisfy $3 \leq p+r \leq 10$), which comprises heating a linear polysiloxane represented by formula (IV):

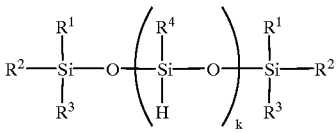

(IV)

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ represents a monovalent substituted or unsubstituted hydrocarbon radical, and k is a number of from 4 to 1,000) and a linear polysiloxane represented by formula (VI):

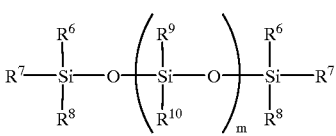

(VI)

(wherein $R^6$ represents a hydroxyl group or a monovalent substituted or unsubstituted hydrocarbon radical, $R^7$ to $R^{10}$ may be the same or different from one another and each represents a monovalent substituted or unsubstituted hydrocarbon radical, and m is a number of from 4 to 1,000), in the presence of a metal alkoxide (claim 9);

the method for producing a cyclic oligosiloxane according to claim 8 or 9, wherein each of $R^1$, $R^4$, $R^5$, $R^7$, $R^8$, $R^9$, $R^{10}$, $R^{11}$ and $R^{12}$ is a methyl group, each of $R^2$ and $R^6$ is a hydroxyl group or a methyl group and $R^3$ is a hydrogen atom or a methyl group (claim 10);

the method for producing a cyclic oligosiloxane according to any one of claims 1 to 10, wherein the metal alkoxide is an aluminum alkoxide, a titanium alkoxide, a zirconium alkoxide, a tin alkoxide or a zinc alkoxide (claim 11);

the method for producing a cyclic oligosiloxane according to any one of claims 1 to 10, wherein the metal alkoxide is an aluminum alkoxide (claim 12); and the method for producing a cyclic oligosiloxane according to any one of claims 1 to 12, wherein the formed cyclic oligosiloxane is distilled under a reduced pressure (claim 13).

(Mode of Carrying out the Invention)

The following describes the present invention in detail.

Each of $R^1$ of the linear polysiloxane represented by the aforementioned formula (I), $R^1$ of the linear polysiloxane represented by the aforementioned formula (IV) and $R^7$ and $R^8$ of the linear polysiloxane represented by the aforementioned formula (VI) is a monovalent substituted or unsubstituted hydrocarbon radical, and examples of the hydrocarbon radical include a halogenated alkyl group, an alkyl group, a cycloalkyl group, an alkenyl group, a cycloalkenyl group and an aryl group. Among these groups, methyl group, ethyl group, propyl group, isopropyl group, n-butyl group, s-butyl group, t-butyl group, cyclohexyl group, vinyl group and phenyl group are preferred, and methyl group and phenyl group are more preferred. Most preferred is methyl group.

Each of $R^2$ of the linear polysiloxane represented by the aforementioned formula (I), $R^2$ of the linear polysiloxane represented by the aforementioned formula (IV) and $R^6$ of the linear polysiloxane represented by the aforementioned formula (VI) is a hydroxyl group or a monovalent substituted or unsubstituted hydrocarbon radical, and examples of the monovalent substituted or unsubstituted hydrocarbon radical are the same as those of the aforementioned $R^1$.

Each of $R^3$ of the linear polysiloxane represented by the aforementioned formula (I) and $R^3$ of the linear polysiloxane represented by the aforementioned formula (IV) is a hydrogen atom or a monovalent substituted or unsubstituted hydrocarbon radical, and examples of the monovalent substituted or unsubstituted hydrocarbon radical are the same as those of the aforementioned $R^1$.

Each of $R^4$ and $R^6$ of the linear polysiloxane represented by the aforementioned formula (I), $R^4$ and $R^6$ of the cyclic polysiloxane represented by the aforementioned formula (II), $R^4$ and $R^6$ of the cyclic oligosiloxane represented by the aforementioned formula (III), $R^4$ of the linear oligosiloxane represented by the aforementioned formula (IV), $R^5$ of the cyclic polysiloxane represented by the aforementioned formula (V), $R^9$ of the linear polysiloxane represented by the aforementioned formula (VI), $R^{11}$ of the cyclic polysiloxane represented by the aforementioned formula (VII), $R^4$, $R^5$, $R^9$ and $R^{11}$ of the cyclic oligosiloxane represented by the aforementioned formula (VIII) and $R^4$ and $R^9$ of the cyclic oligosiloxane represented by the aforementioned formula (IX) is a monovalent substituted or unsubstituted hydrocarbon radical, and its examples are the same as those of the aforementioned $R^1$. In addition, $R^4$ and $R^6$ of the aforementioned formulae (I), (II) and (III) and $R^4$, $R^5$, and $R^9$ and $R^{11}$ of the aforementioned formulae (IV), (V), (VI), (VII), (VIII) and (IX) may be the same or different from one another as respective repeating units.

Each of $R^5$ of the linear polysiloxane represented by the aforementioned formula (I), $R^5$ of the cyclic polysiloxane represented by the aforementioned formula (II), $R^5$ of the cyclic oligosiloxane represented by the aforementioned formula (III), $R^{10}$ of the linear polysiloxane represented by the aforementioned formula (VI), $R^{12}$ of the cyclic polysiloxane represented by the aforementioned formula (VII), $R^{10}$ and $R^{12}$ of the cyclic oligosiloxane represented by the aforementioned formula (VIII) and $R^{10}$ of the cyclic oligosiloxane represented by the aforementioned formula (IX) is a monovalent substituted or unsubstituted hydrocarbon radical, and examples of the hydrocarbon radical include an alkyl group, a cycloalkyl group, an alkenyl group, a cycloalkenyl group and an aryl group. Preferred among these groups include methyl group, ethyl group, a substituted alkyl group represented by $CH_2CH_2X^1$ (wherein $X^1$ represents a monovalent organic group such as a halogen atom, cyano group, phenyl group, an alkoxy group, an alkylcarbonyl group or an alkoxycarbonyl group), a substituted alkyl group represented by $CH_2CH(CH_3)X^2$ (wherein $X^2$ represents a monovalent organic group such as a halogen atom, phenyl group, an alkylcarbonyl group or an alkoxycarbonyl group), a substituted alkyl group represented by $CH_2CH_2CH_2X^3$ (wherein $X^3$ represents a monovalent organic group such as a halogen atom, hydroxyl group or a substituted or unsubstituted alkoxy group), vinyl group and phenyl group. In addition, $R^5$ of the aforementioned formulae (I), (II) and (III) and $R^{10}$ and $R^{12}$ of the aforementioned formulae (VI), (VII), (VIII) and (IX) may be the same or different from one another as respective repeating units.

Illustrative examples of the linear polysiloxane represented by the aforementioned formula (I) include $Me_3SiO$—$(Me_3SiO)_x$—$SiMe_3$,
$Me_3SiO$—$(Ph_2SiO)_x$—$SiMe_3$,
$Me_3SiO$—$(MePhSiO)_x$—$SiMe_3$,
$Me_2PhSiO$—$(Me_2SiO)_x$—$SiMe_2Ph$,
$MePh_2SiO$—$(Me_2SiO)_x$—$SiMePh_2$,
$Me_2Si(OH)O$—$(Me_2SiO)_x$—$SiMe_2(OH)$,
$Me_3SiO$—$(MeHSiO)_x$—$SiMe_3$,
$Me_2PhSiO$—$(MeHSiO)_x$—$SiMe_2Ph$,
$MeHSi(OH)O$—$(MeHSiO)_x$—$SiMe(OH)H$, (wherein x is a number of from 4 to 1,000, preferably from 20 to 500, more preferably from 35 to 200, Me means methyl group and Ph means phenyl group)

$Me_3SiO$—$(MeSi(CH_2CH_2C_6H_4CH_3)O)_5$—$(MeHSiO)_5$—$SiMe_3$,
$MeHSi(OH)O$ —$(MeSi(CH_2CH_2C_6H_4CH_3)O)_5$—$(MeHSiO)_5$—$SiMe(OH)H$,
$Me_3SiO$—$(Me_2SiO)_x$—$(MeHSiO)_y$—$SiMe_3$,
$Me_3SiO$—$(MePhSiO)_x$—$(MeHSiO)_y$—$SiMe_3$,
$Me_3SiO$—$(MeSi(CH_2CH(CH_3)C_6H_5)O)_x$—$(MeHSiO)_y$—$SiMe_3$, and
$Me_3SiO$—$(MeSi(CH_2CH_2CH_2(OCH_2CH_2)_nOMe)O)_x$—$(MeHSiO)_y$—$SiMe_3$ (wherein each of x and y is a number of from 4 to 1,000, preferably x+y is from 20 to 500, more preferably x+y is from 35 to 200, and n is 0 or a number of from 1 to 100, preferably from 1 to 20, more preferably from 5 to 10).

Examples of the cyclic polysiloxane represented by the aforementioned formula (II) include

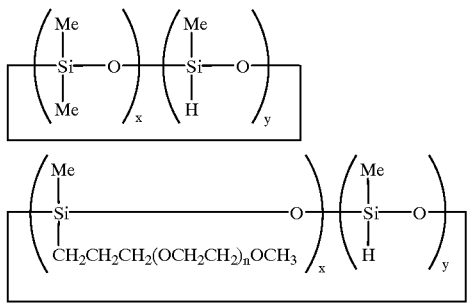

-continued

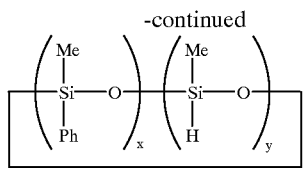

wherein each of x and y is 0 or a number of from 1 to 1,000, preferably x+y is from 4 to 100, more preferably x+y is from 4 to 10, and n is 0 or a number of from 1 to 100, preferably from 1 to 20, more preferably from 5 to 10).

Examples of the cyclic oligosiloxane represented by the aforementioned formula (III) include

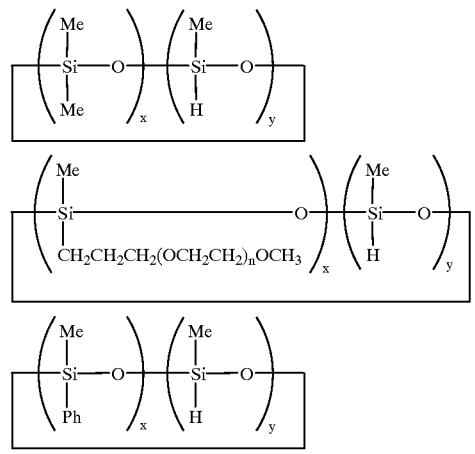

(wherein each of x and y is 0 or a number of from 1 to 10 and x+y is a number of from 3 to 10, preferably each of x and y is 0 or a number of from 1 to 6 and x+y is a number of from 3 to 6, more preferably each of x and y is 0 or a number of from 1 to 4 and x+y is 4, and n is 0 or a number of from 1 to 100, preferably from 1 to 20, more preferably from 5 to 10).

Illustrative examples of the linear polysiloxane represented by the aforementioned formula (IV) include
Me$_3$SiO—(MeHSiO)$_x$—SiMe$_3$,
Me$_2$PhSiO—(MeHSiO)$_x$—SiMe$_2$Ph,
MeHSi(OH)O—(MeHSiO)$_x$—SiMe(OH)H,
Me$_3$SiO—(PhHSiO)$_x$—SiMe$_3$,
Me$_2$PhSiO—(PhHSiO)$_x$—SiMe$_2$Ph and
MeHSi(OH)O—(PhHSiO)$_x$—SiMe(OH)H
(wherein x is a number of from 4 to 1,000, preferably from 20 to 500, more preferably from 35 to 200).

Examples of the cyclic polysiloxane represented by the aforementioned formula (V) include

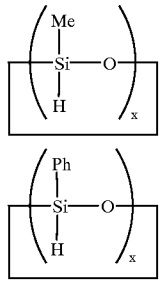

(wherein x is a number of from 4 to 1,000, preferably from 4 to 100, more preferably from 4 to 10).

Examples of the linear polysiloxane represented by the aforementioned formula (VI) include
Me$_3$SiO—(Me$_2$SiO)$_x$—SiMe$_3$,
Me$_3$SiO—(Ph$_2$SiO)$_x$—SiMe$_3$,
Me$_3$SiO—(MePhSiO)$_x$—SiMe$_3$,
Me$_2$PhSiO—(Me$_2$SiO)$_x$—SiMe$_2$Ph,
MePh$_2$SiO—(Me$_2$SiO)$_x$—SiMePh$_2$,
Me$_2$Si(OH)O—(Me$_2$SiO)$_x$—SiMe$_2$(OH) and
Me$_3$SiO—(MeSi(CH$_2$CH$_2$CH$_2$(OCH$_2$CH$_2$)$_n$OMe)O)$_x$—SiMe$_3$
(wherein x is a number of from 4 to 1,000, preferably from 20 to 500, more preferably from 35 to 200, and n is 0 or a number of from 1 to 100, preferably from 1 to 20, more preferably from 5 to 10).

Illustrative examples of the cyclic polysiloxane represented by the aforementioned formula (VII) include

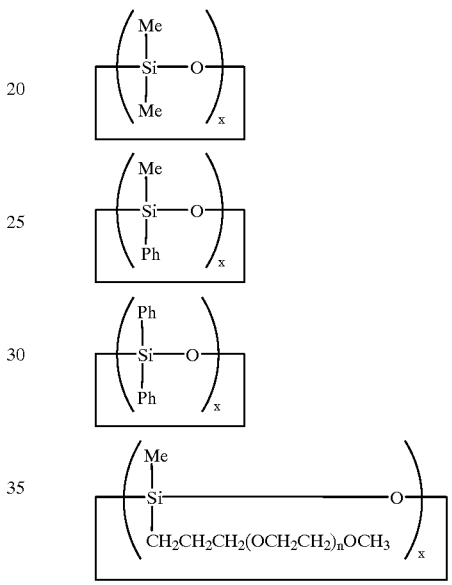

(wherein x is a number of from 4 to 1,000, preferably from 4 to 100, more preferably from 4 to 10, and n is 0 or a number of from 1 to 100, preferably from 1 to 20, more preferably from 5 to 10).

Examples of the cyclic oligosiloxane represented by the aforementioned formulae (VIII) and (IX) include

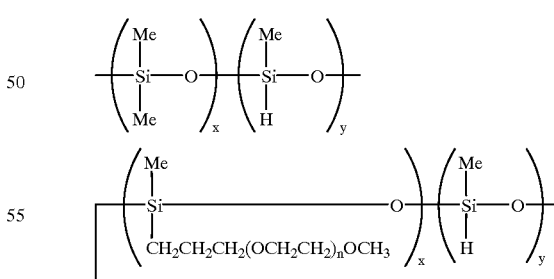

(wherein each of x and y is a number of from 1 to 9 and x+y is a number of from 3 to 10, preferably each of x and y is a number of from 1 to 5 and x+y is a number of from 3 to 6, more preferably each of x and y is a number of from 1 to 3 and x+y is 4, and n is 0 or a number of from 1 to 100, preferably from 1 to 20, more preferably from 5 to 10).

The metal alkoxide to be used in the present invention can be represented for example by the following formula (X):

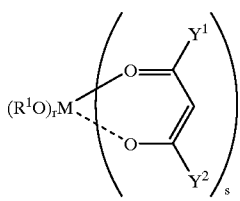

(wherein $R^1$ is a monovalent substituted or unsubstituted hydrocarbon radical and examples of the hydrocarbon radical are the same as those of $R^1$ of the aforementioned formula (I), each of $Y_1$ and $Y^2$ is an alkyl group having 1 to 8 carbon atoms, an aryl group or an alkoxy group, M is a divalent to tetravalent metal element, each of r and s is 0, 1, 2, 3 or 4, and r+s is from 2 to 4). Among these compounds, a metal alkoxide in which M is Al, Ti, Zr, Sn or Zn is used preferably, a metal alkoxide in which M is Al, Ti or Zr, is used more preferably, and an aluminum alkoxide is used most preferably.

Illustrative examples of the metal alkoxide include aluminum triethoxide, aluminum triisopropoxide, aluminum tributoxide, aluminum tri-sec-butoxide, aluminum diisopropoxy-sec-butoxide, aluminum diisopropoxyacetylacetonate, aluminum di-sec-butoxyacetylacetonate, aluminum diisopropoxyethylacetoacetate, aluminum di-sec-butoxyethylacetoacetate, aluminum trisacetylacetonate, aluminum trisethylacetoacetate, aluminum acetylacetonate bisethylacetoacetate, titanium tetraethoxide, titanium tetraisopropoxide, titanium tetrabutoxide, titanium diisopropoxybisacetylacetonate, titanium diisopropoxybisethylacetoacetate, titanium tetra-2-ethylhexyloxide, titanium diisopropoxybis(2-ethyl-1,3-hexanediolate), titanium dibutoxybis(triethanolaminate), zirconium tetrabutoxide, zirconium tetraisopropoxide, zirconium tetramethoxide, zirconium tributoxide monoacetylacetonate, zirconium dibutoxide bisacetylacetonate, zirconium butoxide trisacetylacetonate, zirconium tetraacetylacetonate, zirconium tributoxide monoethylacetoacetate, zirconium dibutoxide bisethylacetoacetate, zirconium butoxide trisethylacetoacetate and zirconium tetraethylacetoacetate. In addition to these compounds, cyclic 1,3,5-triisopropoxycyclotrialuminoxane and the like can also be used. Among these compounds, aluminum triisopropoxide, aluminum tri-sec-butoxide, aluminum diisopropoxyethylacetoacetate, aluminum di-sec-butoxyethylacetoacetate, aluminum trisacetylacetonate, titanium tetraisopropoxide, titanium tetrabutoxide and zirconium tetrabutoxide are used preferably. Most preferred is aluminum triisopropoxide.

These metal alkoxydes may be used either alone or in any combination.

Amount of the metal alkoxide to be used in the present invention can be selected broadly depending on the reaction rate, but it is generally from 0.01 to 10 parts by weight, preferably from 0.01 to 5 parts by weight, more preferably from 0.01 to 1 part by weight, based on the material polysiloxane.

The reaction temperature in the present invention may be any temperature at which the reaction progresses and is generally from 60 to 300° C., but a temperature of from 100 to 200° C. is desirable for the purpose of inhibiting side reactions and accelerating the reaction efficiently.

The reaction of the present invention can be carried out under ordinary pressure or under a reduced pressure, but it is desirable to carry out the reaction under a reduced pressure in order to efficiently promote the reaction at a relatively low temperature by successively distilling the product. In that case, the reaction can be carried out under a reduced pressure of from 10 to 300 mmHg.

As occasion demands, an appropriate solvent can be used in the reaction of the present invention. A solvent which does not have chemical reactivity with the metal alkoxide but has a boiling point of higher than that of the formed cyclic oligosiloxane can be used. Illustrative examples of the solvent include decane, dodecane, mineral oil, mesitylene, diethylene glycol diethyl ether and diethylene glycol dibutyl ether. It can be used in an optional amount.

This reaction can be carried out in the presence of a small amount of an alkoxysilane as an additive agent other than the solvent, but yield of the cyclosiloxane of interest is reduced as the amount of the added alkoxysilane is increased, so that its practical value becomes low.

The reaction of the present invention can be carried out by mixing and heating the material polysiloxane and a metal alkoxide and then purifying the product by distillation or the like means or by successively distilling the product while the reaction is carried out. In order to prevent side reactions, it is desirable to carry out the reaction by successively distilling the product.

When the product is distilled, a rectifying column such as a packed column can be used as occasion demands. When a rectifying column is used, purity of the product can be increased.

According to the reaction of the present invention, a low molecular weight cyclic oligosiloxane can be obtained from a high molecular weight linear or cyclic polysiloxane, but reverse conversion of a low molecular weight compound into a high molecular weight compound can also be carried out. In consequence, in the invention of claims 1, 2, 8 and 9 of this application, the number of constituting silicon atoms of the obtained cyclic oligosiloxane is generally decreased when compared with that of the starting material polysiloxane, but a case in which the number of constituting silicon atoms is increased and a case in which the number of constituting silicon atoms does not change before and after the reaction, such as changes from linear form to cyclic form and changes in substituent groups, are also included in the present invention.

BEST MODE OF CARRYING OUT THE INVENTION

Examples of the present invention are given below by way of illustration and not by way of limitation.

INVENTIVE EXAMPLE 1

A 300 ml capacity three neck round bottom flask equipped with a thermometer, a magnetic stirrer tip, an distillation tube with a rectifying column (Vigreaux type, 15 cm) and an distillation collector was connected to a decompression pump through a trap. The flask was charged with 150 g of a polymethylhydrogensiloxane which is terminated with trimethylsilyl groups represented by $Me_3SiO$—$(MeHSiO)_{40}$—$SiMe_3$ and 1.5 g of aluminum triisopropoxide, and heated for 30 minutes in an oil bath of 150° C. under ordinary pressure. Next, while heating the flask at 150 to 160° C. in the oil bath and keeping the system under a reduced pressure of 100 mmHg, the fraction distilled at an distillation temperature of 65 to 70° C. was recovered over 2 hours, thereby obtaining 113 g of the fraction. The resulting residue was a cloudy liquid. When analyzed by a gas chromatography, the thus obtained fraction showed a composition of 1.8% by weight of 1,3,5-trimethylcyclotrisiloxane, 59.1% by weight of 1,3,5,7-tetramethylcyclotetrasiloxane, 31.5% by weight of 1,3,5,7,9-pentamethylcyclopentasiloxane, 5.7% by weight of 1,3,5,7,9,11-hexamethylcyclohexasiloxane and 1.9% by weight of other high boiling point components.

INVENTIVE EXAMPLE 2

A 1 liter capacity three neck round bottom flask equipped with a thermometer, a magnetic stirrer tip, an distillation tube with a rectifying column (McMahon packing, 30 cm) and a fraction collector was connected to a decompression pump through a trap. The flask was charged with 750 g of a polymethylhydrogensiloxane, which is terminated with trimethylsilyl groups, represented by $Me_3SiO$—$(MeHSiO)_{40}$—$SiMe_3$ and 0.75 g of aluminum triisopropoxide, and heated for 30 minutes in an oil bath of 180° C. under ordinary pressure. Next, while heating the flask at 180 to 190° C. in the oil bath and keeping the system under a reduced pressure of 100 mmHg, the fraction distilled at an distillation temperature of 69 to 78° C. was recovered over 9 hours, thereby obtaining 690 g of the fraction. The resulting residue was a liquid. When analyzed by a gas chromatography, the thus obtained fraction showed a composition of 4.3% by weight of 1,3,5-trimethylcyclotrisiloxane, 82.3% by weight of 1,3,5,7-tetramethylcyclotetrasiloxane and 13.4% by weight of other high boiling point components.

INVENTIVE EXAMPLE 3

A 300 ml capacity three neck round bottom flask equipped with a thermometer, a magnetic stirrer tip, an distillation tube with a rectifying column (Vigreaux type, 15 cm) and a fraction collector was connected to a decompression pump through a trap. The flask was charged with 150 g of a polymethylhydrogensiloxane which is terminated with trimethylsilyl groups having a viscosity of 100 cp, 150 g of a polydimethylsiloxane which is terminated with trimethylsilyl groups having a viscosity of 100 cp and 1.5 g of aluminum triisopropoxide and subjected to 30 minutes of preliminary heating in an oil bath of 150° C. under ordinary pressure. Next, while heating the flask at 150 to 160° C. in the oil bath and keeping the system under a reduced pressure of 50 mmHg, the fraction distilled during the reaction was recovered over 2 hours, thereby obtaining 220 g of the fraction. The resulting residue was a cloudy liquid. Results of gas chromatography and NMR analyses showed that the thus obtained fraction was a cyclosiloxane mixture having 46% of MeHSiO unit and 54% of $Me_2SiO$ unit in average molar fraction and having mostly 3 to 6 siloxy units per 1 molecule.

INVENTIVE EXAMPLE 4

A 30 ml capacity flask equipped with a magnetic stirrer tip and a reflux condenser was charged with 15.0 g of tetramethylcyclotetrasiloxane and 0.15 g of aluminum triisopropoxide and heated in an oil bath of 150° C. under ordinary pressure. One hour thereafter, the reaction solution was analyzed by a gas chromatography to find that 4.8% by weight of pentamethylcyclopentasiloxane and 0.8% by weight of hexamethylcyclohexasiloxane were formed.

COMPARATIVE EXAMPLE

When 50 g of a polymethylhydrogensiloxane which is terminated with trimethylsilyl groups represented by $Me_3SiO$—$(MeHSiO)_{40}$—$SiMe_3$ was put into a 300 ml capacity three neck round bottom flask and a methanol solution of sodium methoxide was added thereto as an alkaline catalyst, decomposition of the material occurred by vigorously generating gas and a part of the reaction system was gelled, so that the reaction could not be continued.

INDUSTRIAL APPLICABILITY

According to the present invention, cyclic oligosiloxane can be produced with high yield by a method having industrially high practical value, by which the reaction can be carried out under moderate conditions, namely neutral condition and relatively low temperature, using easily available materials, without causing gelatin of the reaction system.

What is claimed is:

1. A method for producing a cyclic oligosiloxane, which comprises heating a linear or cyclic polysiloxane containing Si—H group in the presence of a metal alkoxide.

2. A method for producing a cyclic oligosiloxane represented by formula (III):

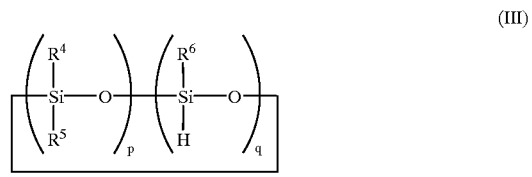

(III)

(wherein $R^4$ to $R^6$ may be the same or different from one another and each represents a monovalent substituted or unsubstituted hydrocarbon radical, p and q are each independently 0 or a number of from 1 to 10, and p and q are also numbers that satisfy $3 \leq p+q \leq 10$), which comprises heating a linear polysiloxane represented by formula (I):

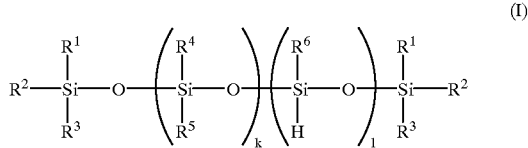

(I)

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ to $R^6$ may be the same or different from one another and each represents a monovalent substituted or unsubstituted hydrocarbon radical, k and l are each independently 0 or a number of from 1 to 1,000, and k and l are also numbers that satisfy $4 \leq k+l \leq 1,000$) and/or a cyclic polysiloxane represented by formula (II):

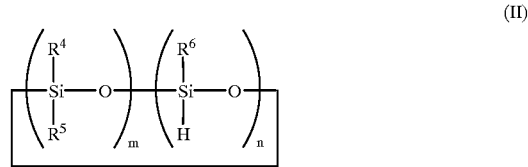

(II)

(wherein $R^4$ to $R^6$ may be the same or different from one another and each represents a monovalent substituted or unsubstituted hydrocarbon radical, m and n are each independently 0 or a number of from 1 to 1,000, and m and n are also numbers that satisfy $3 \leq m+n \leq 1,000$) in the presence of a metal alkoxide.

3. The method for producing a cyclic oligosiloxane according to claim 2, wherein said k and m are each independently 0 or a number of from 1 to 999, said l and n are each independently a number of from 1 to 1,000, said p is 0 or a number of from 1 to 9 and said q is a number of from 1 to 10.

4. The method for producing a cyclic oligosiloxane according to claim 3, wherein said k, l, m, n, p and q are numbers which satisfy $5 \leq m+n \leq 1,000$, $p+q<k+l$ and $p+q<m+n$.

5. The method for producing a cyclic oligosiloxane according to any one of claims 2 to 4, wherein each of said $R^1$, $R^4$ and $R^6$ is a methyl group, $R^2$ is a hydroxyl group or a methyl group and $R^3$ is a hydrogen atom or a methyl group.

6. The method for producing a cyclic oligosiloxane according to any one of claims 2 to 4, wherein said k, l, m, n, p and q are $k<l$, $m<n$ and $p<q$.

7. The method for producing a cyclic oligosiloxane according to any one of claims 3 to 4, wherein $k=m=p=0$.

8. A method for producing a cyclic oligosiloxane represented by formula (VIII):

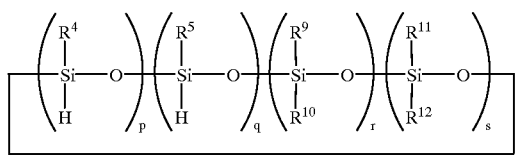

(VIII)

(wherein $R^4$, $R^5$, $R^9$, $R^{10}$, $R^{11}$ and $R^{12}$ may be the same or different from one another and each represents a monovalent substituted or unsubstituted hydrocarbon radical, each of p, q, r and s is a number of from 0 to 9, and p, q, r and s are also numbers that satisfy $3 \leq p+q+r+s \leq 10$, $1 \leq p+q$ and $1 \leq r+s$), which comprises heating (1) a polysiloxane component consisting of a linear polysiloxane represented by formula (IV):

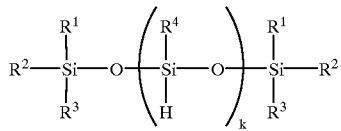

(IV)

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ represents a monovalent substituted or unsubstituted hydrocarbon radical, and k is a number of from 4 to 1,000) and/or a cyclic polysiloxane represented by formula (V):

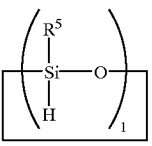

(V)

(wherein $R^5$ represents the same or a different monovalent substituted or unsubstituted hydrocarbon radical, and l is a number of from 4 to 1,000) and (2) a polysiloxane component consisting of a linear polysiloxane represented by formula (VI):

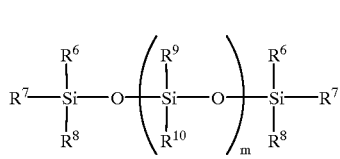

(VI)

(wherein $R^6$ represents a hydroxyl group or a monovalent substituted or unsubstituted hydrocarbon radical, $R^7$ to $R^{10}$ may be the same or different from one another and each represents a monovalent substituted or unsubstituted hydrocarbon radical, and m is a number of from 4 to 1,000) and/or a cyclic polysiloxane represented by formula (VII):

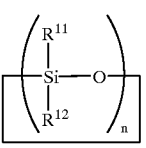

(VII)

(wherein $R^{11}$ and $R^{12}$ may be the same or different from each other and each represents a monovalent substituted or unsubstituted hydrocarbon radical, and n is a number of from 4 to 1,000), in the presence of a metal alkoxide.

9. A method for producing a cyclic oligosiloxane represented by formula (IX):

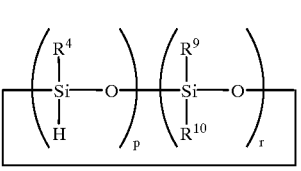

(IX)

(wherein $R^4$, $R^9$ and $R^{10}$ may be the same or different from one another and each represents a monovalent substituted or unsubstituted hydrocarbon radical, each of p and r is a number of from 1 to 9, and p and r are also numbers that satisfy $3 \leq p+r \leq 10$), which comprises heating a linear polysiloxane represented by formula (IV):

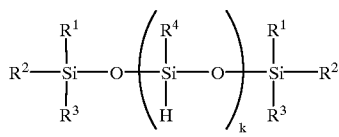

(wherein $R^1$ represents a monovalent substituted or unsubstituted hydrocarbon radical, $R^2$ represents a hydroxyl group or a monovalent substituted or unsubstituted hydrocarbon radical, $R^3$ represents a hydrogen atom or a monovalent substituted or unsubstituted hydrocarbon radical, $R^4$ represents a monovalent substituted or unsubstituted hydrocarbon radical, and k is a number of from 4 to 1,000) and a linear polysiloxane represented by formula (VI):

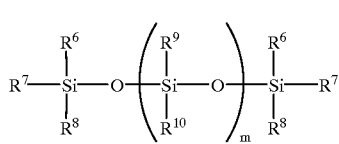

(wherein $R^6$ represents a hydroxyl group or a monovalent substituted or unsubstituted hydrocarbon radical, $R^7$ to $R^{10}$ may be the same or different from one another and each represents a monovalent substituted or unsubstituted hydrocarbon radical, and m is a number of from 4 to 1,000), in the presence of a metal alkoxide.

10. The method for producing a cyclic oligosiloxane according to claim 8 or 9, wherein each of $R^1$, $R^4$, $R^5$, $R^7$, $R^8$, $R^9$, $R^{10}$, $R^{11}$ and $R^{12}$ is a methyl group, each of $R^2$ and $R^6$ is a hydroxyl group or a methyl group and $R^3$ is a hydrogen atom or a methyl group.

11. The method for producing a cyclic oligosiloxane according to any one of claims 1 to 4, 8 and 9, wherein said metal alkoxide is an aluminum alkoxide, a titanium alkoxide, a zirconium alkoxide, a tin alkoxide or a zinc alkoxide.

12. The method for producing a cyclic oligosiloxane according to any one of claims 1 to 4, 8 and 9, wherein said metal alkoxide is an aluminum alkoxide.

13. The method for producing a cyclic oligosiloxane according to any one of claims 1 to 4, wherein the formed cyclic oligosiloxane is distilled under a reduced pressure.

14. The method for producing a cyclic oligosiloxane according to claim 5, wherein said k, l, m, n, p, and q are k<l, m<n and p<q.

15. The method for producing a cyclic oligosiloxane according to claim 5, wherein k=m=p=0.

16. A method for producing a cyclic oligosiloxane, which comprises heating a chain or cyclic polysiloxane in the presence of a metal alkoxide selected from the group consisting of an aluminum alkoxide, a titanium alkoxide, a zirconium alkoxide, a tin alkoxide and a zinc alkoxide.

* * * * *